(12) United States Patent
Thorn

(10) Patent No.: US 11,830,628 B1
(45) Date of Patent: Nov. 28, 2023

(54) EYE MOVEMENT DESENSITIZATION AND REPROCESSING TREATMENT SYSTEM

(71) Applicant: John Thorn, Victor, ID (US)

(72) Inventor: John Thorn, Victor, ID (US)

( * ) Notice: Subject to any disclaimer, the term of this patent is extended or adjusted under 35 U.S.C. 154(b) by 105 days.

(21) Appl. No.: 17/545,508

(22) Filed: Dec. 8, 2021

Related U.S. Application Data

(60) Provisional application No. 63/122,559, filed on Dec. 8, 2020.

(51) Int. Cl.
*G16H 80/00* (2018.01)
*G16H 20/70* (2018.01)
*G16H 40/67* (2018.01)
*G16H 40/63* (2018.01)
*A61M 21/00* (2006.01)

(52) U.S. Cl.
CPC ............ *G16H 80/00* (2018.01); *A61M 21/00* (2013.01); *G16H 20/70* (2018.01); *G16H 40/63* (2018.01); *G16H 40/67* (2018.01); *A61M 2021/0022* (2013.01); *A61M 2021/0027* (2013.01); *A61M 2021/0044* (2013.01); *A61M 2205/3553* (2013.01)

(58) Field of Classification Search
CPC ........ G16H 80/00; G16H 40/67; G16H 40/63; G16H 20/70; A61M 21/00; A61M 2021/0022; A61M 2021/0027; A61M 2021/0044; A61M 2205/3553
USPC ..................................... 240/573.1; 340/573.1
See application file for complete search history.

(56) References Cited

U.S. PATENT DOCUMENTS

| | | | |
|---|---|---|---|
| 5,384,593 A | 1/1995 | Gell, Jr. et al. | |
| 5,619,291 A | 4/1997 | Putnam | |
| 5,953,102 A | 9/1999 | Berry | |
| 6,425,764 B1 | 7/2002 | Lanson | |
| 9,449,528 B1 | 9/2016 | Lugaresi | |
| 9,510,765 B2 * | 12/2016 | Greder | A61B 5/6803 |
| 9,668,930 B2 | 6/2017 | Surenthiran | |
| 9,833,184 B2 | 12/2017 | Derchak | |
| 9,924,271 B2 | 3/2018 | Lai et al. | |
| 10,537,702 B2 | 1/2020 | Weiss et al. | |

(Continued)

*Primary Examiner* — Zhen Y Wu
(74) *Attorney, Agent, or Firm* — CRAMER PATENT & DESIGN, PLLC; Aaron R. Cramer

(57) ABSTRACT

An eye movement desensitization and reprocessing treatment system comprises an apparatus designed for the remote administration of eye movement desensitization and reprocessing (EMDR) therapy via an internet connection. The eye movement desensitization and reprocessing treatment system enables a therapist to remotely present a patient with a plurality of varying visual, audible, and tactile stimuli. The eye movement desensitization and reprocessing treatment system utilizes a pair of visual goggles with two layers of glass or glass-like material, which displays a visual image for the patient to follow with their eyes. A camera system provides a visual feed of the patient's face on the therapist's goggles. The frame of the visual screen comprises an array of LED lights that provide simulated sequential movement Over the ear noise cancelling headphones are also provided. A pair of vibration units are configured to be held in the patient's left and right hand and are synchronized with the apparent motion of the LED lights. The device is battery operated and interfaces via Bluetooth® with an internet enabled electronic device.

16 Claims, 4 Drawing Sheets

(56) References Cited

U.S. PATENT DOCUMENTS

| | | | |
|---|---|---|---|
| 2008/0234601 A1* | 9/2008 | Wexelman | A61B 5/163 600/558 |
| 2009/0156886 A1* | 6/2009 | Burgio | A61B 5/6805 607/45 |
| 2016/0228771 A1* | 8/2016 | Watson | A63F 13/285 |
| 2018/0004478 A1* | 1/2018 | Chen | G06F 3/1454 |
| 2018/0018827 A1* | 1/2018 | Stafford | A63F 13/69 |
| 2018/0348863 A1* | 12/2018 | Aimone | A61B 5/378 |
| 2019/0200920 A1* | 7/2019 | Tien | A61B 5/0205 |
| 2019/0227329 A1* | 7/2019 | Han | G02B 27/0179 |
| 2019/0331928 A1* | 10/2019 | Lin | G02C 11/08 |
| 2019/0374742 A1* | 12/2019 | Hanbury | A61M 21/00 |
| 2020/0041790 A1* | 2/2020 | Martinez | G02B 27/148 |
| 2020/0086077 A1* | 3/2020 | Gazit | A61H 5/00 |
| 2020/0376230 A1* | 12/2020 | Causey | A61M 21/02 |
| 2021/0149199 A1* | 5/2021 | Guan | G02B 5/04 |

\* cited by examiner

EYE MOVEMENT DESENSITIZATION AND REPROCESSING TREATMENT SYSTEM

RELATED APPLICATIONS

The present invention was first described in and claims the benefit of U.S. Provisional Application No. 63/122,559 filed Dec. 8, 2020, the entire disclosures of which are incorporated herein by reference.

FIELD OF THE INVENTION

The present invention relates to a method of treatment for Post-Traumatic Stress Disorder (PTSD) utilizing Eye Movement Desensitization and Reprocessing (EMDR) therapy.

BACKGROUND OF THE INVENTION

Post-Traumatic Stress Disorder (PTSD) affects tens of millions of people worldwide, with approximately eight million (8M) cases identified each year in the United States. PTSD results from experiencing, or witnessing, terrifying events that threaten annihilation over which the victim or witness has no control.

Most commonly associated with the violence of war, the ravages of natural disasters, the trauma of serious personal illness or pandemic, PTSD also results from the verbal, emotional, social and physical abuse experienced by millions of children living in dysfunctional homes of domestic violence, the instability of transitory foster or custodial care placements, or the deprivation of refugee relocation centers.

Research has established EMDR as one of the most efficient and effective treatments available for PTSD. EMDR does not rely on the techniques and methods of traditional psychotherapies. Rather, EMDR involves the rhythmic, back and forth movement of the patient's eyes, crossing the midline of their visual field with each repetition, effectively dampening the emotional impact of the trauma, and reprocessing the traumatic memories so they no longer produce PTSD symptoms.

Research has shown that simultaneously crossing the midline in the visual, auditory and tactile sensory channels, optimizes the therapeutic effect of EMDR treatment. The EMDR treatment device described herein provides the means by which EMDR treatment may be delivered to meet the demands PTSD places on health care providers in either the traditional face-to-face setting of the physical office, or as the Covid-19 pandemic has made increasingly necessary, online in the virtual office.

SUMMARY OF THE INVENTION

The inventor has recognized the aforementioned, inherent problems and lack in the art and observed that there is a need for an EMDR treatment system having a headset which has a laminated screen, a patient's computer adapted to be used by a patient, a therapist's computer adapted to be used by a therapist, a left-hand vibrating unit and a right-hand vibrating unit given to the patient that are utilized in an EMDR therapy session, a plurality of light-emitting diodes projecting a dot image on a reflective glass through a lens, an elastic head strap working together with a pair of temple pieces accommodates a plurality of different sized patients, a plurality of foam padding fitted on top a brow-piece of the headset to provide a comfortable fit; and a pair of ear speakers mounted on the pair of temple pieces to allow the patient to receive auditory stimuli synchronized with the visual and tactile sensory input during the EMDR therapy session, as well as to communicate with the therapist. The patient's computer communicating with a computer network. The therapist's computer communicates with the computer network to communicate directly with the patient's computer, the therapist is adapted to view a face and a pair of eyes of the patient on the therapist's computer.

The headset may communicate with the patient computer via a plurality of wireless signals. The wireless signals may also be used to communicate with the left-hand vibrating unit and the right-hand vibrating unit. The patient may look forward to the laminated screen incorporated in the headset where they encounter the reflective glass on an interior side of the laminated screen. The laminated screen may allow the patient to focus on the dot image concurrently with focusing on the therapist to obtain a reflection-free view of the pair of patient eyes and a plurality of eye movements and facial features essential to conducting the EDMR therapy session in the therapist's computer over the Internet.

An exterior side of the laminated screen may be made of a non-reflective glass and is intended to face the patient's computer. The laminated screen may be made of glass. The computer network may be the Internet. The patient computer may communicate with the Internet via a long-range RF signal. The long-range RF signal is a Wi-Fi signal. The long-range RF signal may be a cellular signal. The patient's computer may be located anywhere on earth. The therapist's computer may be located anywhere on earth. The headset, the left-hand vibrating unit, and the right-hand vibrating unit may be powered by one or more rechargeable batteries.

The headset, the left-hand vibrating unit, and the right-hand vibrating unit may include one or more wireless transmitters for wireless operation. The one or more wireless transmitters may be one or more Bluetooth® transmitters. One or more video conferencing capabilities of the patient's computer captures movement of one of the pair of the eyes of the patient. The light-emitting diodes may be arranged in a linear fashion. The light-emitting diodes may be illuminated in a sequential manner, side-to-side, where the patient interprets them as a single moving dot image. The EMDR treatment system may remotely administer an EMDR therapy over an Internet connection adapted by the patient's computer and the therapist's computer each accessing a non-transitory storage medium.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTIVE KEY

Figure 1:
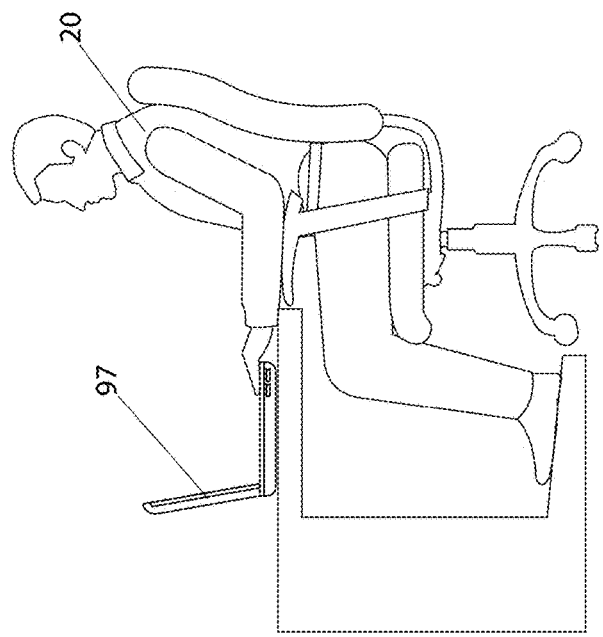
FIG. 1 is a pictorial view of the EMDR treatment system, shown in a utilized state, according to the preferred embodiment of the present invention.
Figure 1:
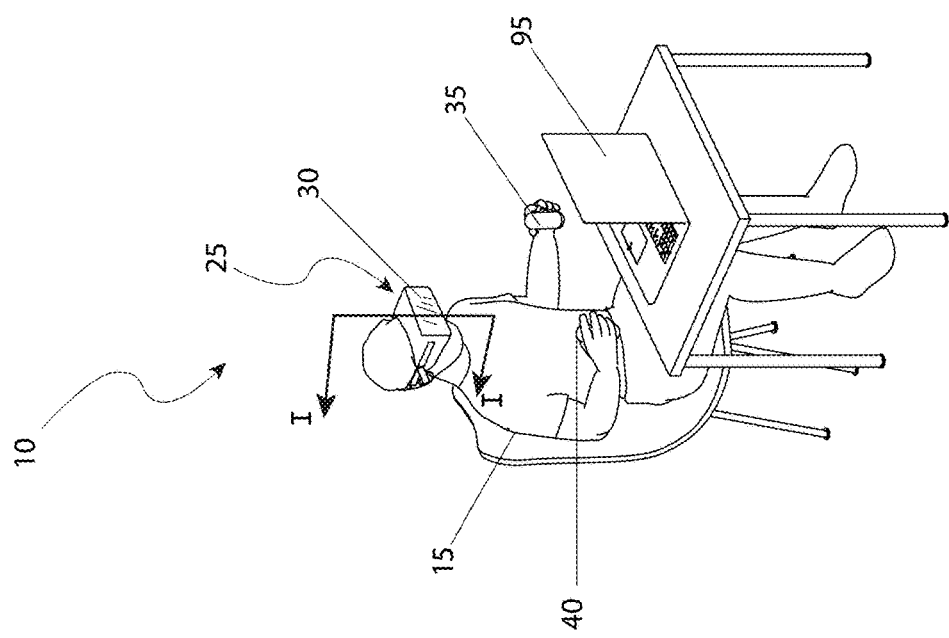

10 EMDR treatment system
15 patient 20 therapist
25 headset
30 laminated screen
35 left-hand vibrating unit
40 right-hand vibrating unit
45 eye
50 reflective glass
55 non-reflective glass
60 light-emitting diodes (LED's)
62 lens
65 dot image
75 temple piece
80 ear speaker
85 head strap
90 foam padding
95 patient's computer
97 therapist's computer
100 wireless signal
105 Internet
110 long range RF signal

DESCRIPTION OF THE INVENTION

The best mode for carrying out the invention is presented in terms of its preferred embodiment, herein depicted within FIGS. 1 through 4. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope. All of the implementations described below are exemplary implementations provided to enable persons skilled in the art to make or use the embodiments of the disclosure and are not intended to limit the scope of the disclosure, which is defined by the claims.

The terms "a" and "an" herein do not denote a limitation of quantity, but rather denote the presence of at least one (1) of the referenced items.

1. Detailed Description of the Figures

Referring now to FIG. 1, a pictorial view of the EMDR treatment system 10, shown in a utilized state, according to the preferred embodiment of the present invention is disclosed. The EMDR treatment system 10 provides for the remote administration of EMDR therapy over an Internet connection provided by a patient's computer 95 and a therapist's computer 97 each accessing a non-transitory storage medium. The system 10 accommodates a patient 15 and a therapist 20 located independently anywhere in the world. The patient 15 wears a headset 25 that incorporates a laminated screen 30, preferably fabricated out of glass, while viewing the patient's computer 95, while the therapist 20 views the face and eyes of the patient 15 on the therapist's computer 97. The headset 25 is provided with specialized features that will be described in greater detail herein below. The patient 15 is also provided with a left-hand vibrating unit 35 and a right-hand vibrating unit 40 which are also utilized in the EMDR therapy session. The headset 25, the left-hand vibrating unit 35, and the right-hand vibrating unit 40 are all powered by rechargeable batteries (preferably recharged by USB power) and are provided with wireless transmitters for wireless operation (preferably Bluetooth®). Further description of the interconnecting features of the system 10 will be described below.

Figure 2:
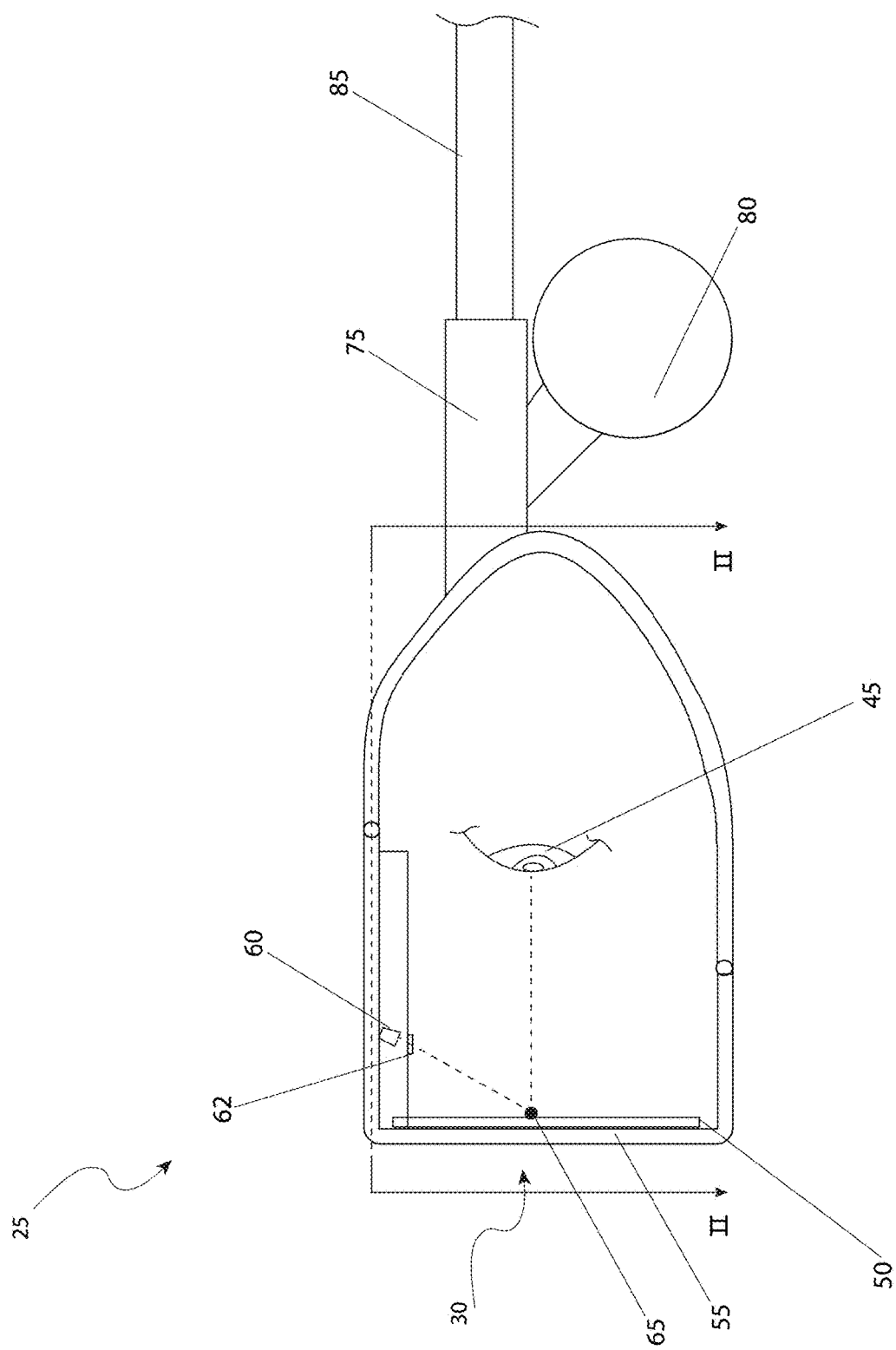
FIG. 2 is a sectional view of the headset, as seen along a Line I-I, as shown in FIG. 1, according to the preferred embodiment of the present invention.

Referring next to FIG. 2, a sectional view of the headset 25, as seen along a Line I-I, as shown in FIG. 1, according to the preferred embodiment of the present invention is depicted. The eye 45 of the patient 15 (as shown in FIG. 1) looks forward to the laminated screen 30 incorporated in the headset 25 where they encounter a reflective glass 50 on the interior side of the laminated screen 30. The exterior side of the laminated screen 30 is of a non-reflective glass 55 (also seen in FIG. 3) and is intended to face the patient's computer 95 (as shown in FIG. 1). This configuration allows the patient 15 to focus on a dot image 65 concurrently with focusing on the therapist 20 (as shown in FIG. 1) to obtain a reflection-free view of the patient's eyes 45 and the eye movements and facial features essential to conducting effective EDMR during the EDMR therapy session in the therapist's computer 97 over the Internet 105 (as shown in FIG. 4). Further description of the dot image 65 is provided below.

A set of light-emitting diodes (LED's) 60, arranged in a linear fashion, (of which only one (1) is shown, due to illustrative limitations) project a dot image 65 on the reflective glass 50 through a lens 62. These light-emitting diodes (LED's) 60 are illuminated in a sequential manner, side-to-side, where the patient 15 interprets them as a single moving dot image 65. The video conferencing capabilities of the patient's computer 95 (as shown in FIG. 1) captures the movement of the eye 45 of the patient 15. Two (2) temple pieces 75, (of which only one (1) is shown due to illustrative limitations) support two (2) comfortable ear speakers 80, (of which only one (1) is shown due to illustrative limitations). An elastic head strap 85, working together with the temple pieces 75 provide for a comfortable, secure, and a light but tight fit.

Figure 3:
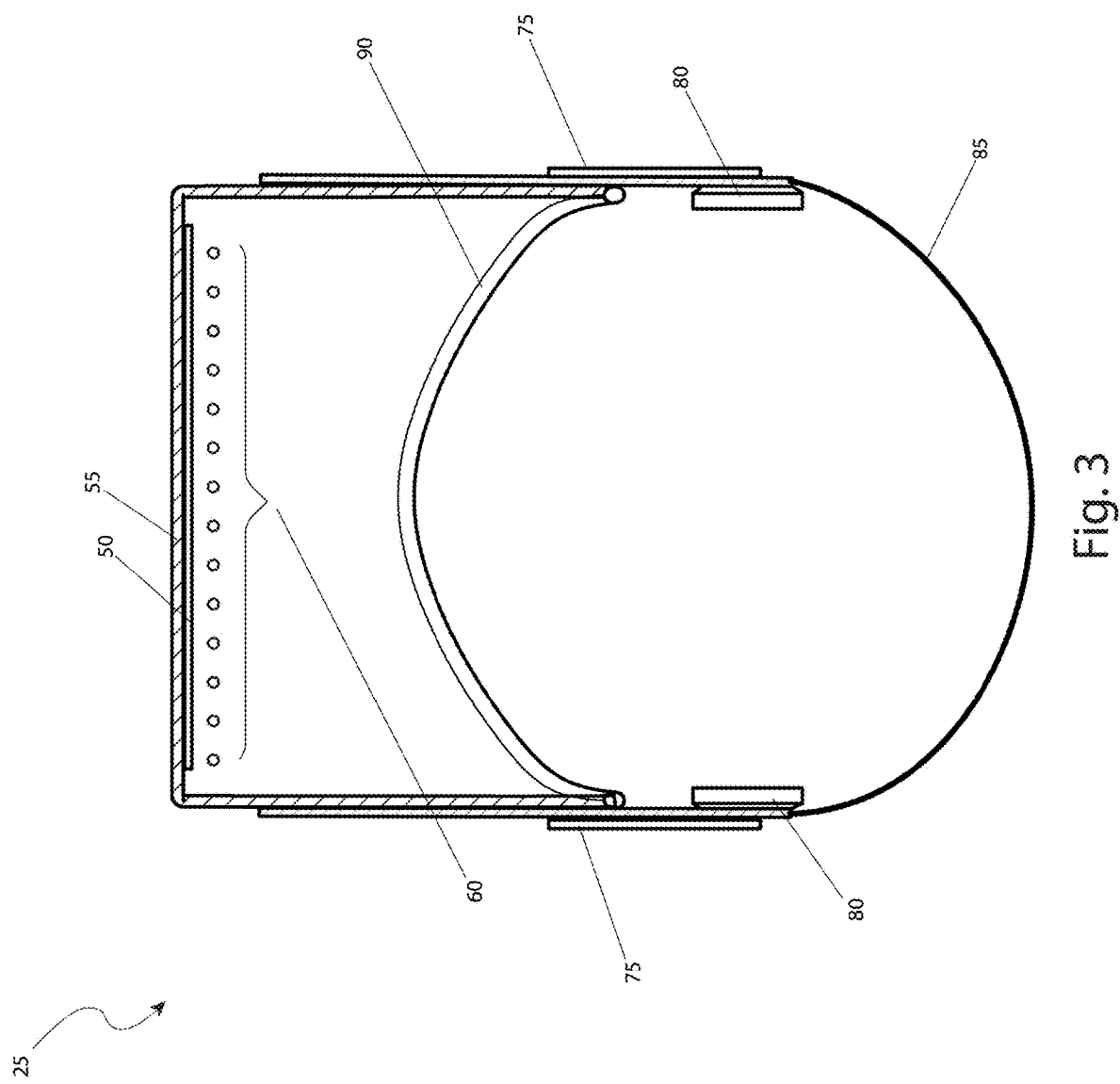
FIG. 3 is a sectional view of the headset, as seen along a Line II-II, as shown in FIG. 2, according to the preferred embodiment of the present invention.
Figure 4:
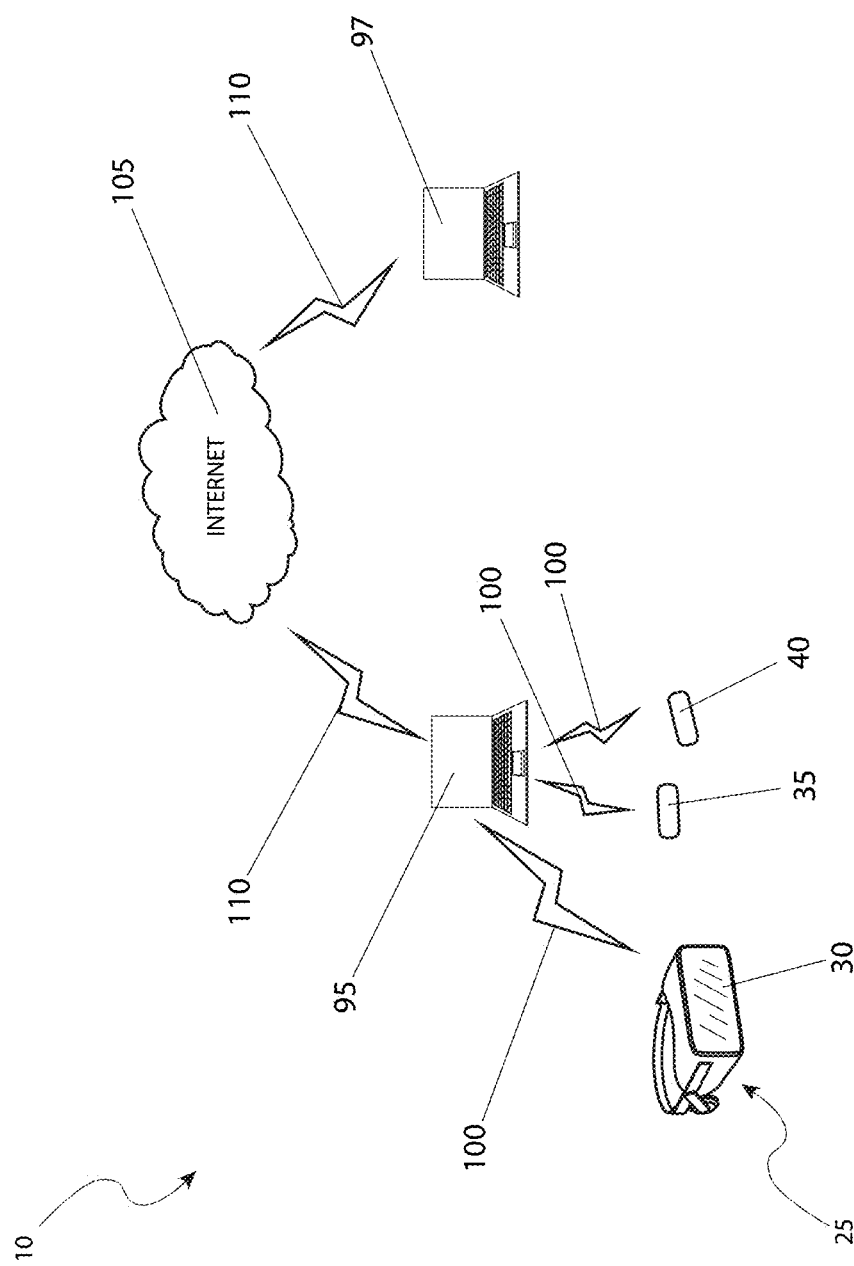
FIG. 4 is an intercommunication diagram depicting major electronic components of the EMDR treatment system, according to the preferred embodiment of the present invention.

Referring now to FIG. 3, a sectional view of the headset 25, as seen along a Line II-II, as shown in FIG. 2, according to the preferred embodiment of the present invention is shown. This view clearly shows the linear arrangement of the multiple light-emitting diodes (LED's) 60 with respect to the reflective glass 50 and the non-reflective glass 55, preferably located about the brow area of the headset 25. The foam padding 90 is fitted top the brow-piece of the headset 25 to provide a comfortable fit. The two (2) ear speakers 80 mounted on the two (2) temple pieces 75 allow the patient 15 (as shown in FIG. 1) to receive auditory stimuli synchronized with the visual and tactile sensory input during the EMDR therapy session, as well as to communicate with the therapist 20, (as shown in FIG. 1). The elastic nature of the head strap 85 ensures that it will fit all sizes of patients 15.

Referring to FIG. 4, an intercommunication diagram depicting major electronic components of the EMDR treatment system 10, according to the preferred embodiment of the present invention is disclosed. The headset 25 communicates with a patient computer's 95 via wireless signals 100. Likewise, wireless signals 100 are also used to communicate with the left-hand vibrating unit 35 and the right-hand vibrating unit 40. The patient computer's 95 then communicates with the Internet 105 via a long-range RF signal 110 such as Wi-Fi or cellular. On the therapist 20 side, communication with the Internet 105 is also handled via a long-range RF signal 110, to the therapist's computer 97. It is expected that dedicated non-transitory storage medium are run on both the patient's computer 95 and the therapist's computer 97 to handle communication protocols, security, logging, and other aspects of device 10 operation.

2. Operation of the Preferred Embodiment

The preferred embodiment of the present invention can be utilized by the common user in a relatively effortless manner with some moderate training, typically by the therapist 20, a licensed medical health care provider, or a specialist trained in EMDR therapy session. It is envisioned that the EMDR treatment system 10 would be constructed in general accordance with FIG. 1 through FIG. 4. The user would procure the system 10 from conventional procurement channels such as markets that cater to health care professionals, mail order and Internet supply houses and the like.

After procurement and prior to utilization, the EMDR treatment system 10 would be prepared in the following manner: a communication link to and from the patient's computer 95 and the therapist's computer 97 would be established using wireless signals 100 and long range RF signal 110 as described above; the patient 15 would place the headset 25 on their head and adjust the head strap 85 and the ear speakers 80 for a comfortable fit and providing them with a direct view through the laminated screen 30 of the patient's computer 95 (please see FIG. 1); the therapist 20 would connect or initiate a video conference to the patient 15 via the therapist's computer 97. At this point in time, the EMDR treatment system 10 is ready for utilization.

During utilization of the EMDR treatment system 10, the following procedure would be initiated: the patient 15 would follow the dot image 65 on the reflective glass 50 in the headset 25 as directed by the therapist 20 via the ear speakers 80; the therapist 20 is provided a live image of the movement of the eyes 45 of the patient 15 via the video conference shared on the therapist's computer 97; the non-reflective glass 55 provides for the therapist 20 having a clear view of the patient's eyes 45 by eliminating reflections of the patient's 25 environment, including the reflection of the patient's computer 95 screen on the headset 25 that would otherwise impair the therapist's 20 view of the patient's 25 eyes 45 which is critical to an effective EMDR therapy session; the therapist 20 may then effectively synchronize the stopping and starting of movement of the eyes 45 of the patient 15 as appropriate with the visual clues perceived by the therapist 20; the ear speakers 80 are synchronized with the left-right movement of the dot image 65 on the reflective glass 50 of the headset 25 to present the patient 15 with auditory stimulus that is synchronized with the visual; and, the therapist 20 may communicate audibly with the patient 15 via the video conferencing abilities of the patient's computer 95 and the therapist's computer 97 to facilitate clear communication during the procedure. In a similar manner, the left-hand vibrating unit 35 and the right-hand vibrating unit 40 are also synchronized with the left-right "movement" of the light and sound as controlled by the therapist 20.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

The invention claimed is:

1. An eye movement desensitization and reprocessing (EMDR) treatment system, comprising:
   a headset having a laminated screen;
   a patient's computer adapted to be used by a patient, the patient's computer communicating with a computer network;
   a therapist's computer adapted to be used by a therapist, the therapist's computer communicating with the computer network to communicate directly with the patient's computer, the therapist is adapted to view a face and a pair of eyes of the patient on the therapist's computer;
   a left-hand vibrating unit and a right-hand vibrating unit given to the patient that are utilized in an EMDR therapy session;
   a plurality of light-emitting diodes projecting a dot image on a reflective glass through a lens;
   an elastic head strap working together with a pair of temple pieces to accommodate a plurality of different sized patients;
   a plurality of foam padding fitted on top of a brow-piece of the headset to provide a comfortable fit; and
   a pair of ear speakers mounted on the pair of temple pieces to allow the patient to receive auditory stimuli synchronized with the visual and tactile sensory input during the EMDR therapy session, as well as to communicate with the therapist;
   wherein the patient looks forward to the laminated screen incorporated in the headset where the patient encounters the reflective glass on an interior side of the laminated screen;
   wherein the laminated screen allows the patient to focus on the dot image concurrently with focusing on the therapist to obtain a reflection-free view of the pair of patient eyes and a plurality of eye movements and facial features essential to conducting the EDMR therapy session in the therapist's computer over an Internet;
   wherein an exterior side of the laminated screen is made of a non-reflective glass and is intended to face the patient's computer; and
   wherein the laminated screen is made of glass.

2. The EMDR treatment system, according to claim 1, wherein the headset communicates with the patient computer.

3. The EMDR treatment system, according to claim 2, wherein the patient computer is used to communicate with the left-hand vibrating unit and the right-hand vibrating unit.

4. The EMDR treatment system, according to claim 1, wherein the computer network is the Internet.

5. The EMDR treatment system, according to claim 1, wherein the patient computer then communicates with the Internet via a long-range radio frequency (RF) technology.

6. The EMDR treatment system, according to claim 5, wherein the long-range RF technology is a Wi-Fi technology.

7. The EMDR treatment system, according to claim 5, wherein the long-range RF technology is a cellular technology.

8. The EMDR treatment system, according to claim 1, wherein the patient's computer is located anywhere on earth.

9. The EMDR treatment system, according to claim 1, wherein the therapist's computer is located anywhere on earth.

10. The EMDR treatment system, according to claim 1, wherein the headset, the left-hand vibrating unit, and the right-hand vibrating unit are powered by one or more rechargeable batteries.

11. The EMDR treatment system, according to claim 1, wherein the headset, the left-hand vibrating unit, and the right-hand vibrating unit include one or more wireless transmitters for wireless operation.

12. The EMDR treatment system, according to claim 11, wherein the one or more wireless transmitters are one or more Bluetooth transmitters.

13. The EMDR treatment system, according to claim 1, wherein one or more video conferencing capabilities of the patient's computer captures movement of one of the pair of the eyes of the patient.

14. The EMDR treatment system, according to claim 1, wherein the light-emitting diodes are arranged in a linear fashion.

15. The EMDR treatment system, according to claim 14, wherein the light-emitting diodes are illuminated in a sequential manner, side-to-side, where the patient interprets them as a single moving dot image.

16. The EMDR treatment system, according to claim 1, wherein the EMDR treatment system remotely administers an EMDR therapy over an Internet connection adapted by the patient's computer and the therapist's computer each accessing a non-transitory storage medium.

\* \* \* \* \*